United States Patent
Herzog

(10) Patent No.: US 10,786,260 B2
(45) Date of Patent: Sep. 29, 2020

(54) MEDICAL DEVICE

(71) Applicant: BOSTON SCIENTIFIC SCIMED, INC., Maple Grove, MN (US)

(72) Inventor: Phil Herzog, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 193 days.

(21) Appl. No.: 15/835,182

(22) Filed: Dec. 7, 2017

(65) Prior Publication Data

US 2018/0153555 A1 Jun. 7, 2018

Related U.S. Application Data

(60) Provisional application No. 62/431,421, filed on Dec. 7, 2016.

(51) Int. Cl.
*A61B 17/12* (2006.01)
*A61M 25/06* (2006.01)
(Continued)

(52) U.S. Cl.
CPC .... *A61B 17/12172* (2013.01); *A61B 17/1204* (2013.01); *A61B 17/1214* (2013.01); *A61B 17/12031* (2013.01); *A61B 17/12109* (2013.01); *A61B 17/12122* (2013.01); *A61M 25/0074* (2013.01); *A61M 25/0662* (2013.01); *A61B 17/3415* (2013.01); *A61B 2017/00292* (2013.01); *A61B 2017/00526* (2013.01);
(Continued)

(58) Field of Classification Search
CPC ........ A61B 17/12172; A61B 17/12031; A61B 17/1204; A61B 17/12109; A61B 17/12122; A61B 17/1214; A61M 25/0662; A61M 25/0075; A61M 25/0102; A61M 2025/0079; A61M 2025/0063; A61M 2025/0177; A61M 25/0067; A61M 25/0068; A61M 25/09041
USPC ........................................................ 604/104
See application file for complete search history.

(56) References Cited

U.S. PATENT DOCUMENTS 5,653,684 A 8/1997 Laptewicz et al.
6,015,423 A 1/2000 Andrese
(Continued)

FOREIGN PATENT DOCUMENTS

EP 1606002 A1 12/2005
WO 2012091809 A1 7/2012

OTHER PUBLICATIONS

International Search Report and Written Opinion dated Mar. 26, 2018 for International Application No. PCT/US2017/065169.

*Primary Examiner* — Brandy S Lee
*Assistant Examiner* — Nidah M Hussain
(74) *Attorney, Agent, or Firm* — Seager, Tufte & Wickhem, LLP

(57) ABSTRACT

A medical device comprising an elongated tubular member having a proximal portion, a distal portion, an outer surface and a lumen and the distal portion of the elongated tubular member comprising an expandable occlusion tip, the expandable occlusion tip having a central lumen and comprising a plurality of lobes, the expandable occlusion tip having an unexpanded state and an expanded state, in the unexpanded state the lobes extend distally from the elongated tubular member, in the expanded state, the lobes radially expand and are adapted to restrict flow in a patient's vessel.

3 Claims, 15 Drawing Sheets

(51) Int. Cl.
  *A61M 25/00* (2006.01)
  *A61B 17/22* (2006.01)
  *A61B 17/00* (2006.01)
  *A61M 25/10* (2013.01)
  *A61B 17/34* (2006.01)
  *A61M 25/01* (2006.01)

(52) U.S. Cl.
  CPC ............. *A61B 2017/1205* (2013.01); *A61B 2017/22084* (2013.01); *A61B 2017/22094* (2013.01); *A61M 25/005* (2013.01); *A61M 25/0009* (2013.01); *A61M 25/0045* (2013.01); *A61M 25/0051* (2013.01); *A61M 2025/0177* (2013.01); *A61M 2025/0197* (2013.01); *A61M 2025/1052* (2013.01)

(56) References Cited

U.S. PATENT DOCUMENTS

| | | |
|---|---|---|
| 6,582,400 B1 | 6/2003 | Hawk et al. |
| 7,144,386 B2 | 12/2006 | Korkor et al. |
| 8,066,757 B2 | 11/2011 | Ferrera et al. |
| 8,070,791 B2 | 12/2011 | Ferrera et al. |
| 8,197,493 B2 | 6/2012 | Ferrera et al. |
| 8,574,262 B2 | 11/2013 | Ferrera et al. |
| 8,585,713 B2 | 11/2013 | Ferrera et al. |
| 8,945,143 B2 | 2/2015 | Ferrera et al. |
| 9,320,532 B2 | 4/2016 | Ferrera et al. |
| 9,387,098 B2 | 7/2016 | Ferrera et al. |
| 9,561,345 B2 | 2/2017 | Garrison et al. |
| 9,597,171 B2 | 3/2017 | Shrivastava et al. |
| 2002/0010476 A1 | 1/2002 | Mulholland et al. |
| 2004/0073230 A1 | 4/2004 | Mulholland et al. |
| 2004/0193140 A1* | 9/2004 | Griffin .............. A61M 25/0051 604/524 |
| 2004/0244440 A1 | 12/2004 | Durazzani |
| 2005/0149110 A1 | 7/2005 | Wholey et al. |
| 2006/0264972 A1 | 11/2006 | Mulholland et al. |
| 2007/0244440 A1 | 10/2007 | Pal et al. |
| 2008/0255652 A1 | 10/2008 | Thomas et al. |
| 2009/0264859 A1* | 10/2009 | Mas ................. A61M 25/0074 604/509 |
| 2011/0160757 A1 | 6/2011 | Ferrera et al. |
| 2012/0065660 A1 | 3/2012 | Ferrera et al. |
| 2014/0074144 A1 | 3/2014 | Shrivastava et al. |
| 2014/0155981 A1 | 6/2014 | Ferrera et al. |
| 2015/0057639 A1 | 2/2015 | Storbeck et al. |
| 2015/0209058 A1 | 7/2015 | Ferrera et al. |
| 2016/0106562 A1 | 4/2016 | Puckett, Jr. et al. |
| 2016/0206319 A1* | 7/2016 | Bodewadt ........ A61B 17/12031 |
| 2016/0228684 A1 | 8/2016 | Martin |
| 2016/0256180 A1 | 9/2016 | Vale et al. |
| 2017/0020555 A1 | 1/2017 | Ferrera et al. |
| 2017/0035437 A1* | 2/2017 | Sarge .............. A61B 17/12172 |
| 2017/0105743 A1 | 4/2017 | Vale et al. |
| 2017/0156744 A1 | 6/2017 | Shrivastava et al. |
| 2017/0312020 A1 | 11/2017 | Harlev et al. |
| 2017/0333060 A1 | 11/2017 | Panian |

\* cited by examiner

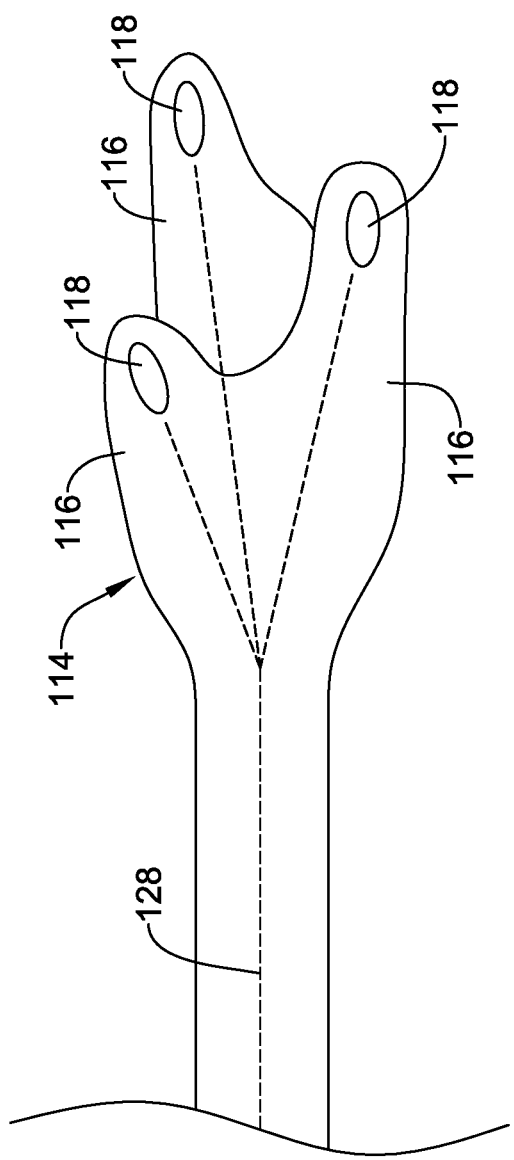

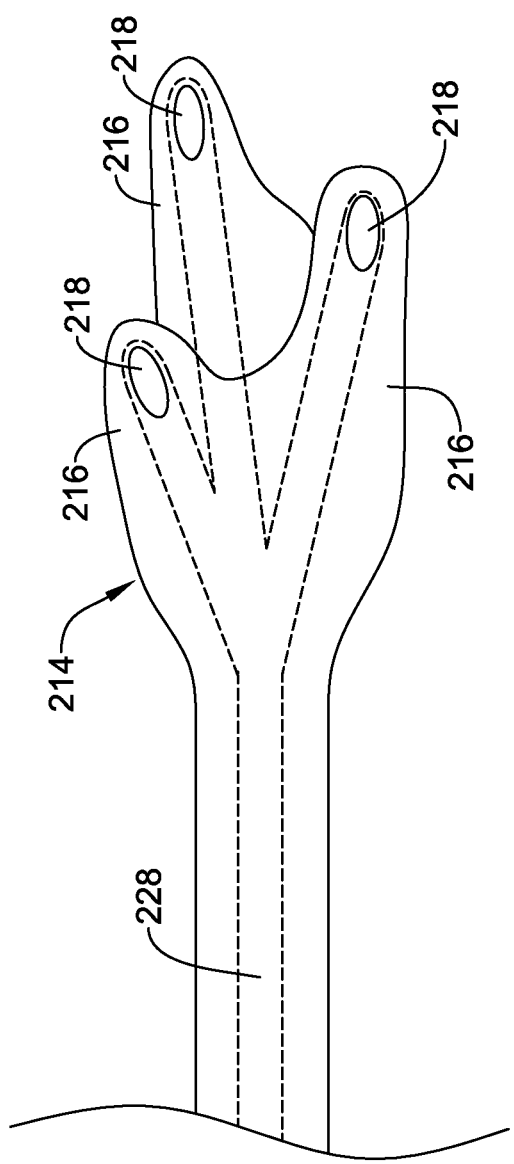

MEDICAL DEVICE

CROSS-REFERENCE TO RELATED APPLICATIONS

This application claims the benefit of priority under 35 U.S.C. § 119 to U.S. Provisional Application Ser. No. 62/431,421, filed Dec. 7, 2016, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, for example, catheters having expandable occlusion tips, and methods for manufacturing and using such devices.

BACKGROUND

A wide variety of devices have been developed for medical use, for example, intravascular use. Some of these devices include guidewires, catheters, and other such devices that each has certain features and characteristics. Among the known medical devices, each has certain advantages and disadvantages. There is an ongoing need to provide alternative designs and methods for making and using medical devices with desirable characteristics and features.

BRIEF SUMMARY

This disclosure provides design, material, manufacturing method, and use alternatives for medical devices.

In one aspect, the disclosure relates to a medical device comprising an elongated tubular member having a proximal portion, a distal portion, an outer surface and a lumen and the distal portion of the elongated tubular member comprising an expandable occlusion tip, the expandable occlusion tip having a central lumen and comprising a plurality of lobes, the expandable occlusion tip having an unexpanded state and an expanded state, in the unexpanded state the lobes extend distally from the elongated tubular member, in the expanded state, at least some of the lobes radially expand and are adapted to restrict flow in a patient's vessel.

Alternatively or additionally to any of the embodiments above, the lobes radially expand and are adapted to restrict retrograde flow in a patient's vessel.

Alternatively or additionally to any of the embodiments above, each of the plurality of lobes comprises an eyelet.

Alternatively or additionally to any of the embodiments above, the medical device further comprises a guidewire, the guidewire extending through the lumen of the elongated tubular member, and in the unexpanded state of the expandable occlusion tip, the guidewire extending through the eyelet of each of the plurality of lobes.

Alternatively or additionally to any of the embodiments above, the expandable occlusion tip comprises three or more lobes.

Alternatively or additionally to any of the embodiments above, the expandable occlusion tip has a size ratio between the expanded state and the unexpanded state that is about 3:1 to about 4:1.

Alternatively or additionally to any of the embodiments above, each of the plurality of lobes is solid in cross-section, wherein at least some of the lobes comprise an eyelet, each eyelet comprising an opening therethrough.

Alternatively or additionally to any of the embodiments above, the elongated tubular member comprises a plurality of apertures defined therein.

Alternatively or additionally to any of the embodiments above, the elongated tubular member comprises a polymer material, and the expandable occlusion tip comprises a polymer material that is the same or different than that of the elongated tubular member.

Alternatively or additionally to any of the embodiments above, all of the lobes radially expand and are adapted to restrict flow in a patient's vessel.

Alternatively or additionally to any of the embodiments above, the expandable occlusion tip comprises a metal frame defining the plurality of lobes.

Alternatively or additionally to any of the embodiments above, the metal frame of the expandable occlusion tip comprises a shape memory material.

In another aspect, the disclosure relates to a catheter assembly comprising an elongated tubular member including a proximal portion, a distal portion, an outer surface and a lumen, and the distal portion of the elongated tubular member comprising an expandable occlusion tip, the expandable occlusion tip comprising a plurality of lobes, wherein at least some of the plurality of lobes comprise an eyelet designed to receive a retention device, wherein the expandable occlusion tip has an unexpanded state and an expanded state, wherein when the expandable occlusion tip is in the unexpanded state, the lobes extend distally from the elongated tubular member and wherein when the expandable occlusion tip in the expanded state, wherein at least some of the lobes radially expand and are adapted to restrict flow within a body lumen.

Alternatively or additionally to any of the embodiments above, the catheter assembly further comprises the retention device, the retention device is a guidewire extending through the lumen of the elongated tubular member, and in the unexpanded state of the expandable occlusion tip, the guidewire extending through the eyelet of each of the plurality of lobes.

Alternatively or additionally to any of the embodiments above, the expandable occlusion tip comprises three or more lobes.

Alternatively or additionally to any of the embodiments above, expandable occlusion tip in the expanded state to the unexpanded state has a size ratio of about 3:1 to about 4:1.

Alternatively or additionally to any of the embodiments above, each of the plurality of lobes is solid in cross-section, wherein at least some of the lobes comprise an eyelet, each eyelet comprising an opening therethrough.

Alternatively or additionally to any of the embodiments above, the elongated tubular member comprises a metal hypotube, the hypotube comprising a plurality of apertures defined therein.

Alternatively or additionally to any of the embodiments above, the elongated tubular member comprises a first polymer material and the expandable occlusion tip comprises a second polymer material that is different than that first polymer material.

Alternatively of additionally to any of the embodiments above, all of the lobes radially expand and and are adapted to restrict flow within a body lumen.

Alternatively or additionally to any of the embodiments above, the expandable occlusion tip comprises a metal frame defining the plurality of lobes.

In another aspect, the disclosure relates to a method of treating a body lumen, the method comprising advancing a catheter through the body lumen toward a treatment site, the catheter comprising an elongated tubular member including a proximal portion and a distal portion and defining an outer surface and a lumen and the distal portion of the elongated tubular member comprising an expandable occlusion tip, the expandable occlusion tip comprising a plurality of lobes, each of the plurality of lobes comprising an eyelet, the expandable occlusion tip having an unexpanded configuration, in the unexpanded configuration the lobes extend distally from the elongated tubular member, and a guidewire extending through the lumen of the elongated tubular member and into the eyelet of each of the plurality of lobes, wherein the guidewire extends through the eyelet of each of the plurality of lobes to hold the expandable occlusion tip in the unexpanded configuration and retracting the guidewire to shift the expandable occlusion tip from the unexpanded configuration to an expanded configuration to radially expand the plurality of lobes to restrict flow.

Alternatively or additionally to any of the embodiments above, the method further comprises injecting contrast fluid, embolent, or both during the advancing step and while the expandable occlusion tip is in the unexpanded configuration.

Alternatively or additionally to any of the embodiments above, the method comprises pre-loading the guidewire in the elongated tubular member through the expandable occlusion tip and into the eyelet of each of the plurality of lobes.

In another aspect, the disclosure relates to a medical device comprising an elongated tubular member having a proximal portion, a distal portion, an outer surface and a lumen and the distal portion of the elongated tubular member comprising an expandable occlusion tip, the expandable occlusion tip having a central lumen and comprising a plurality of lobes, the central lumen of the expandable occlusion tip is in fluid communication with the lumen of the elongated tubular member, the expandable occlusion tip having an unexpanded state and an expanded state, in the unexpanded state the lobes extend distally from the elongated tubular member, in the expanded state, the lobes radially expand and are adapted to restrict flow in a patient's vessel.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 5 is a side view of an example medical device with parts shown in phantom;

FIG. 6 is a side view of an example medical device with parts shown in phantom;

Figure 1:
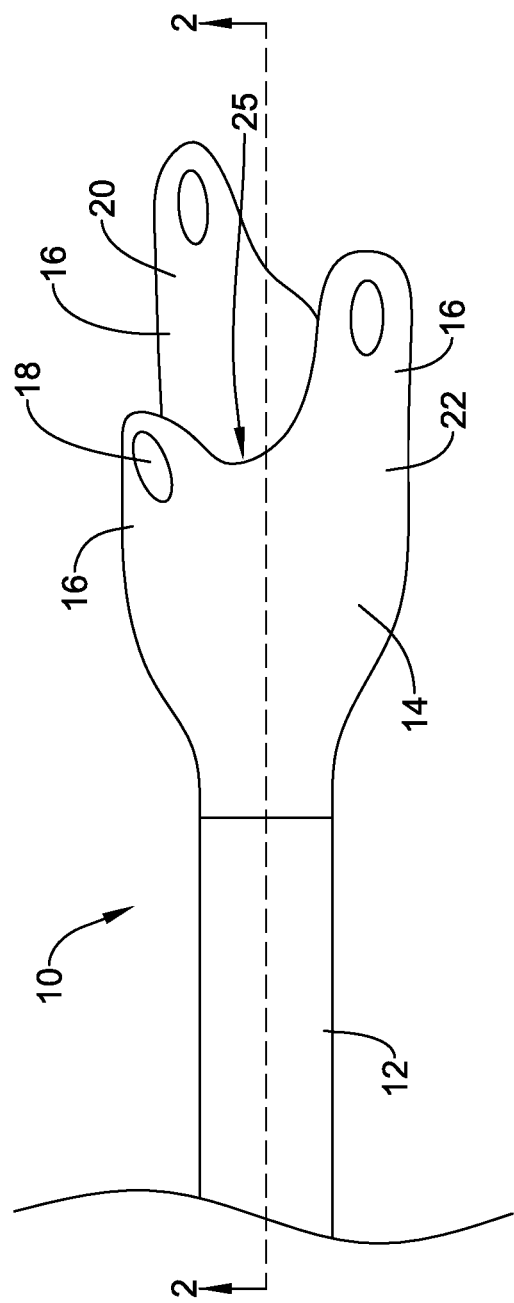
FIG. 1 is a side view of an example medical device in an expanded state.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the disclosure.

As used herein, the terms "proximal" and "distal" refer to that which is closest to the user such as a surgeon and that which is furthest from the user respectively.

Many existing catheters do not restrict the flow of fluid media, for example, the retrograde flow of therapeutic agents, contrast media or embolent, slurries of particles and gels within the vasculature. Retrograde flow of fluid results in fluid flowing back along the catheter into the vessel in the opposite direction to that desired. When injecting contrast media, for example, this can lead to difficulties in identifying the tissue that the subselected artery feeds, and when injecting embolent or other therapeutic agents, it may lead to the destruction of healthy tissue adjacent to tumors, fibroids or other lesions intended for treatment.

The present disclosure relates to catheters assemblies, for example, microcatheter assemblies, designed to at least partially restrict flow. A microcatheter may have an outer diameter in the range of about 1 to about 4 French. However, the present disclosure may be applied to any of a variety of medical devices including, but not limited to, guide catheters, diagnostic catheters, drug delivery catheters, fluid delivery devices, or other infusion or aspiration devices. Depending on the application, sizes in terms of diameter and length may vary widely, depending upon the desired properties of a particular device. For example, in some devices, lengths may range from about 1-300 centimeters or more, while outside diameters may range from about 1 French to about 20 French, or even more in some embodiments.

A side view of an exemplary catheter 10, for example, a microcatheter, is illustrated in FIG. 1. The catheter 10 includes a catheter shaft 12 and an expandable occlusion tip 14 shown in an expanded state. The expandable occlusion tip 14 includes a plurality of lobes 16, for example, two, three, four, five, six or more lobes 16. The catheter 10 is depicted in FIG. 1 with three lobes 16. Some or each lobe 16 may include an eyelet 18 which is designed for insertion of a retention device, such as a guidewire, mandrel, tube, for example, a hypotube or a smaller microcatheter, or other device therethrough (shown in FIG. 3).

Figure 3:
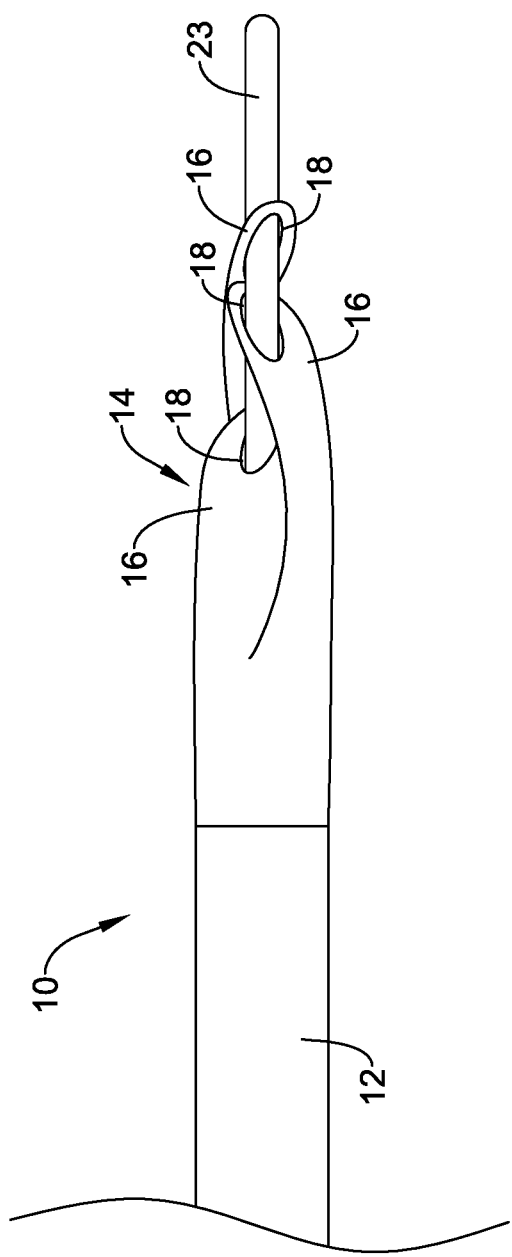
FIG. 3 is a side view of an example medical device in an undeployed state.

The lobes 16 may be spaced uniformly about the longitudinal axis 2-2 of the device. Each lobe 16 may extend distally at various lengths from a distal end 27 of the catheter shaft 12, as shown in various embodiments in FIGS. 1A-1C, so as to allow a retention device 23 to easily thread through each eyelet 18 respectively to hold the expandable occlusion tip 14 in an unexpanded or undeployed and folded state, as shown in FIG. 3 discussed below. The expandable occlusion tip 14 may be formed with pre-defined folds to aid in crimping and folding of the lobes 16 during production. The lobes 16 are illustrated herein as having a leaf or petal-like shape. However, other geometric shapes such as triangular, curvilinear triangular, and the like may be contemplated herein.

The expandable occlusion tip 14 includes a central lumen 25. The central lumen 25 is in fluid communication with the catheter shaft lumen 24. The expandable occlusion tip 14 has an inner surface 20 and an outer surface 22. The expandable occlusion tip 14 in the expanded state may form a convex outer surface 22 and concave inner surface 20 such as a cup or bowl, flower shape, for example, a tulip having a plurality of petals, a conical shape, and the like. The expandable occlusion tip 14 may be formed in the expanded state, for example, by molding, such that the expandable occlusion tip 14 is biased toward the expanded state, which will be discussed in more detail below. The expandable occlusion tip 14 may be formed from a variety of polymer materials, for example, polyesters, polyamides, polyolefins, shape memory polymers, copolymers and terpolymers thereof. The expandable occlusion tip 14 may be formed from the same polymer material or a different polymer material than that of the catheter shaft 12 including any of the polymer materials listed above. In some embodiments, the expandable occlusion tip 14 and the catheter shaft 12 are both formed of at least one layer of a polyether-block-amide copolymer. Other suitable polymer materials for forming both the catheter shaft 12 and the expandable occlusion tip 14 are discussed in more detail below.

Figure 1A:
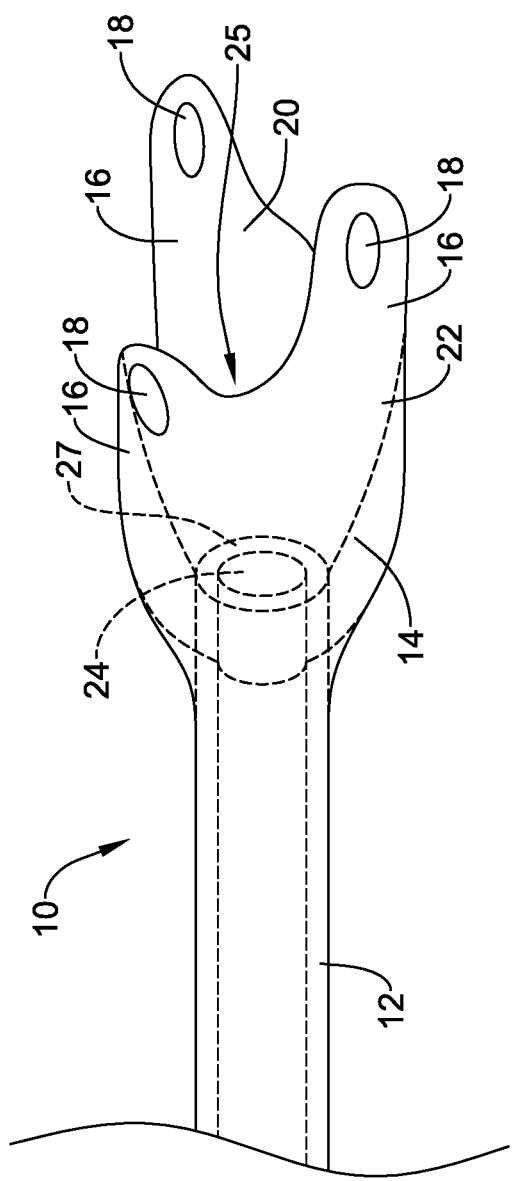
FIG. 1A is a side view of an example medical device in an expanded state with internal parts in phantom.
Figure 1B:
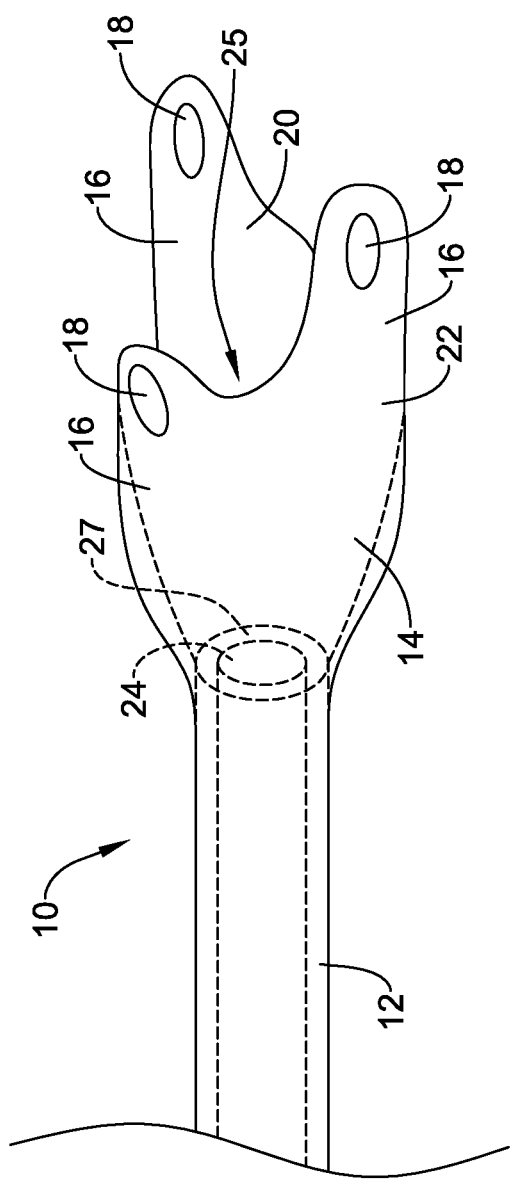
FIG. 1B is a side view of an example medical device in an expanded state with parts shown in phantom.
Figure 1C:
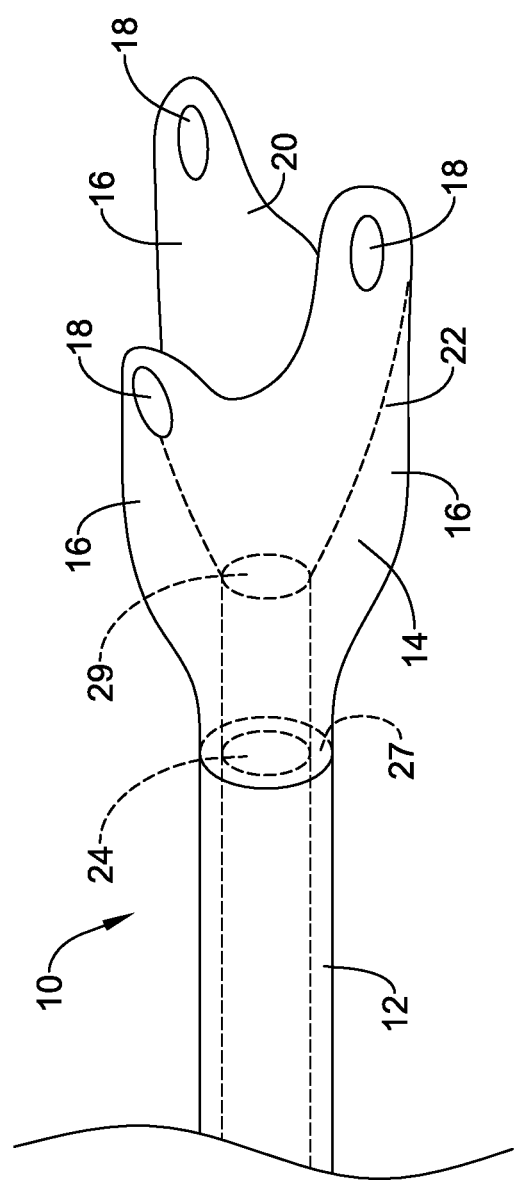
FIG. 1C is a side view of an example medical device in an expanded state with parts shown in phantom.

FIGS. 1A-1C are side views illustrating several ways of securing the expandable occlusion tip 14 to the catheter shaft 12. With respect to FIG. 1A, the expandable occlusion tip 14 is secured to the catheter shaft 12 at a point that is proximal from the distal end 27 of the catheter shaft 12 with the distal portion of the catheter shaft 12 extending into the lumen 25 of the expandable occlusion tip 14 and in fluid communication with the central lumen 25 of the expandable occlusion tip 14, the inner surface 20 of the expandable occlusion tip 14 forming a central concave opening or central lumen 25.

FIG. 1B illustrates an alternative embodiment wherein the expandable occlusion tip 14 is attached to the distal end 27 of the catheter shaft 12, for example, by a butt joint. As such, the distal end 27 of the catheter shaft 12 and the proximal end of the expandable occlusion tip 14 are co-terminus, and the lumen 24 of the catheter shaft 12 being co-terminus with the central lumen 25 of the expandable occlusion tip 14.

FIG. 1C illustrates another alternative embodiment wherein the expandable occlusion tip 14 is formed with a proximal portion 29 which includes a diameter which generally matches the diameter of the lumen 24 of the catheter shaft 12, and a distal portion or the central lumen 25 which includes a larger diameter.

The expandable occlusion tip 14 may be secured to the catheter shaft 12 using a variety of methods known in the art, for example, by over molding the expandable occlusion tip 14 onto the catheter shaft 12, by molding the expandable occlusion tip 14, for example, by injection molding, and then adhering or welding the expandable occlusion tip 14 onto the catheter shaft 12, or by forming the expandable occlusion tip 14 and the catheter shaft 12 integrally.

Figure 2:
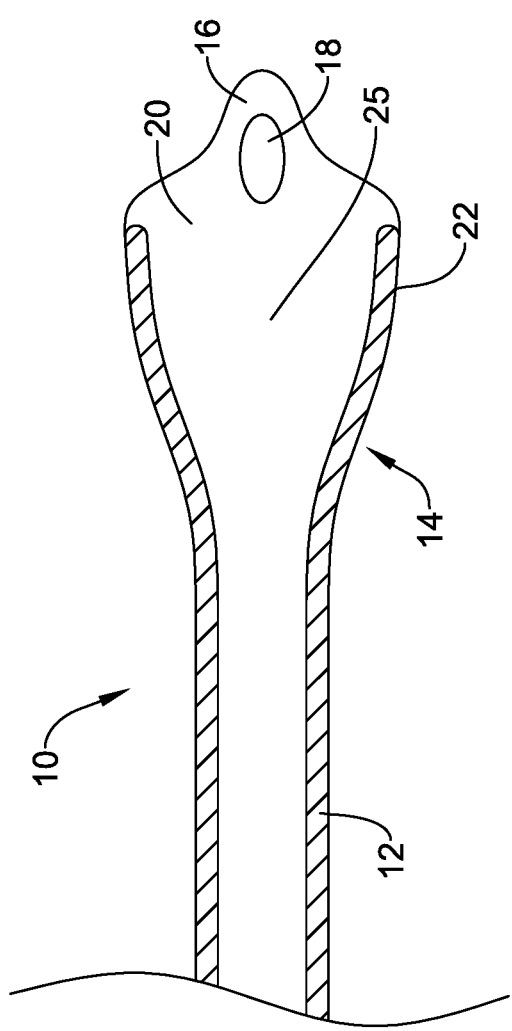
FIG. 2 is a longitudinal cross-section of an example medical device taken at section 2-2 in FIG. 1.

FIG. 2 is a longitudinal cross-section taken at section 2-2 of FIG. 1. The expandable occlusion tip 14 has the inner surface 20 and the outer surface 22, the inner surface 20 of the expandable occlusion tip 14 being concave and forming a conical shape, a cup or bowl, a flower, for example, a tulip shape having a plurality of petals, and so forth. FIG. 2 illustrates the inner surface 20 of the expandable occlusion tip 14 forming a central concave opening or central lumen 25 and a convex outer surface 22.

A side view of the catheter 10 is illustrated in FIG. 3 having a catheter shaft 12 with the expandable occlusion tip 14 shown in an unexpanded or undeployed and folded state. A retention device, for example, a guidewire 23 is disposed in the catheter shaft 12 and extends through the expandable occlusion tip 14 and is disposed through the eyelet 18 of each lobe 16 to maintain the expandable occlusion tip 14 in the unexpanded or undeployed and folded state until delivery and deployment wherein the expandable occlusion tip 14 expands to the expanded state at a treatment site. As discussed above, in these embodiments, each lobe 16 extends from the distal end of the catheter shaft 12 at respectively different distances so as to allow the retention device or guidewire 23 to more easily thread through each eyelet 18 of each lobe 16 respectively. In other embodiments, one or more of the lobes 16 of the expandable occlusion tip 14 may extend at the same distance if desired.

In some embodiments, the retention device, which may be a guidewire 23, a mandrel, a tube, a wire, a rod, and the like, is pre-loaded into the catheter 10, and the assembly may then be packaged, stored and shipped. In some embodiments, the catheter 10 is packaged with a hypotube that has an outer diameter than is less than the inner diameter of the microcatheter, and the hypotube has an inner diameter that is greater than the outer diameter of a guidewire.

The catheter 10 may be delivered to a treatment site with the retention device, for example, a guidewire 23, which maintains the expandable occlusion tip 14 in the undeployed and folded state during delivery through a body lumen.

Figure 4:
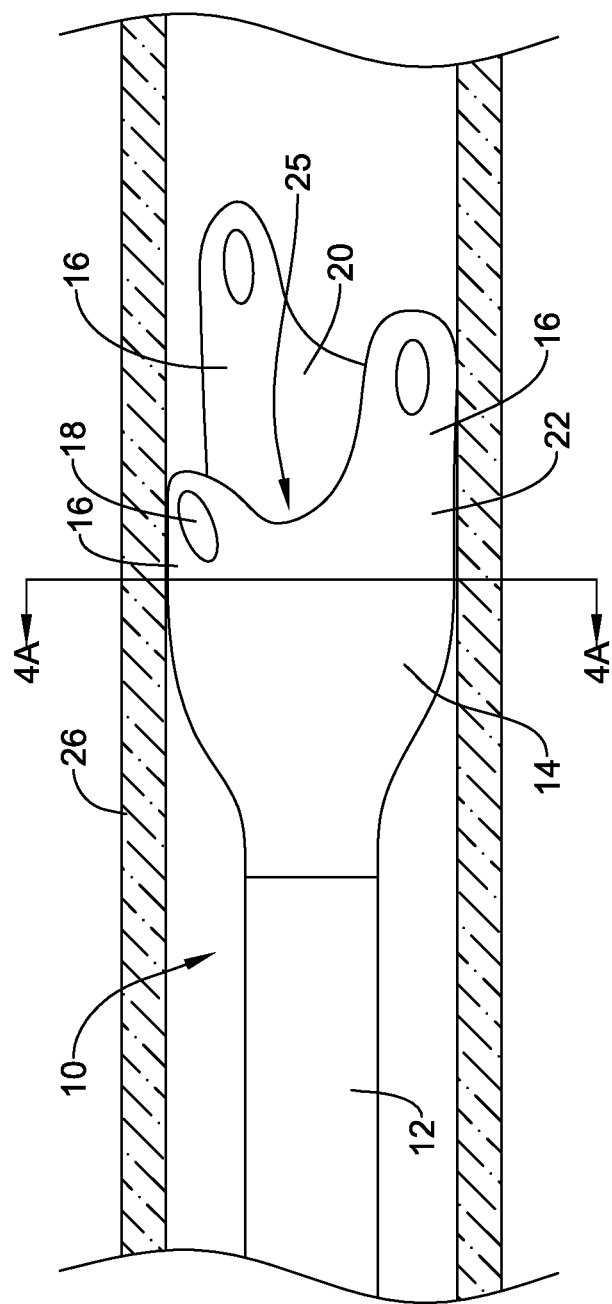
FIG. 4 is a side view of an example medical device in an expanded state in a body vessel.
Figure 4A:
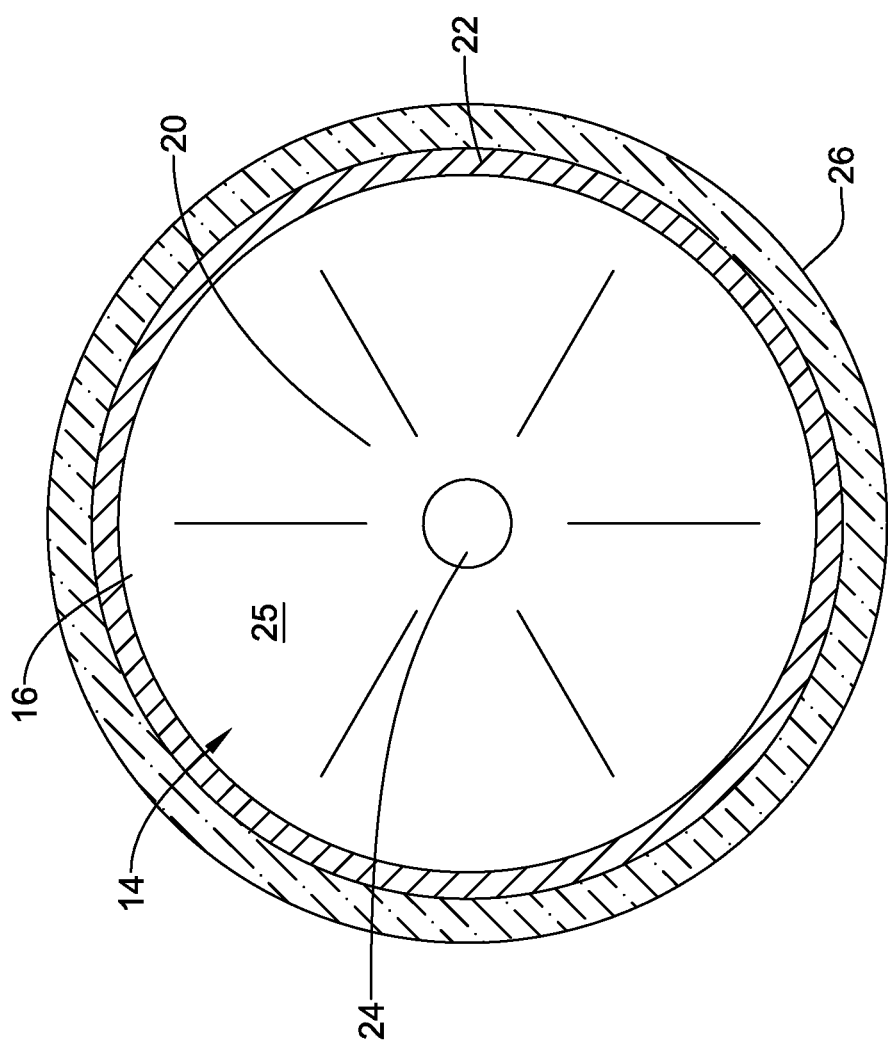
FIG. 4A is a cross-sectional view of an example medical device taken at section 4A-4A of FIG. 4.

A side view of an exemplary catheter 10 is illustrated in FIG. 4 having a catheter shaft 12 with the expandable occlusion tip 14 within a body vessel 26 after retraction of the guidewire 23 which releases and deploys the expandable occlusion tip 14 which allows it to radially expand. The expandable occlusion tip 14 in the expanded state is designed such that expandable occlusion tip 14 and the lobes 16 thereof, conform to the body vessel 26 to restrict flow, for example, between the outer surface of the catheter 10 and the inner surface of a body lumen. For example, retrograde flow of therapeutic agents, contrast media or embolent as well as other fluids that may be injected through the catheter 10 may be restricted. Each lobe 16 has a solid cross-section, wherein at least some of the lobes comprise an eyelet 18, each eyelet 18 comprising an opening therethrough, and the inner surface 20 of the expandable occlusion tip 14 may be exposed to body fluids when in a body lumen. FIG. 4A is a radial cross-section taken at section 4A-4A in FIG. 4. In some embodiments, the expandable occlusion tip 14 may be configured to expand to the same diameter or to a slightly larger diameter than that of the inner diameter of the body lumen so as to occlude the lumen of the body vessel 26 as shown in FIG. 4A. The expandable occlusion tip 14 may also be employed for reducing thrombus in an artery or removing material from a body lumen, for example, kidney stones from the kidney.

In some embodiments, the expandable occlusion tip 14 in the expanded state to the unexpanded state has a size ratio of about 3:1 to about 4:1. For example, if expandable occlusion tip 14 is in the range of about 1 to about 4 French in the unexpanded state, in the expanded state the expandable occlusion tip 14 may be in the range of about 3 French to about 16 French. In some embodiments, the expandable occlusion tip 14 is about 2.8 French in the unexpanded state and in the range of about 8.4 to about 11.2 French in the expanded state. In the unexpanded state, the expandable occlusion tip 14 may be about the same size as that of the catheter shaft 12.

FIGS. 5 and 6 illustrate other example medical devices wherein the expandable occlusion tip 114 is formed with an expandable metal frame 128 shown in phantom. The frame may be a self-expanding frame that is formed from a shape memory metal such as a nickel-titanium alloy of the like. The frame 128 may have a plurality of fingers or the like extending into each lobe 116 as shown in FIG. 5, or the frame 228 may be formed so as to take on a shape similar to that of the expandable occlusion tip 214 and the plurality of lobes 216 as shown in FIG. 6. These frame configurations are exemplary and the scope of the present disclosure is not limited to these configurations, as other configurations are contemplated. The metal frame 128, 228 may provide improved conformance to the inner diameter of a patient's body vessel, improved apposition, an improved seal or fit to the body vessel and better resistance to flow, improved radiopacity to provide easier placement in the body vessel, and can resist collapse of the expandable occlusion tip 114, 214.

The metal frame 128 may also take the form of a loop that lines the distal rim of the expandable occlusion tip 114, or a loop lining the radios of the expandable occlusion tip 114.

The metal frame 128 may be embedded in the tip material or lining the inside of the tip material. The metal frame 128 may be located proximally of each eyelet 118 but distally of the tapered section of the expandable occlusion tip 114.

The expandable occlusion tip 114, 214 may be over molded onto the frame 128, 228 wherein the frame 128, 228 is embedded in the polymeric material of the expandable occlusion tip 114, 214, or the expandable occlusion tip 114, 214 and the frame 128, 228 may be formed separately, and the expandable occlusion tip 114, 214 adhered to or welded thereon.

Eyelets 118, 218 are similar to eyelets 18. A retention device, for example, a guidewire 23 extends through the expandable occlusion tip 114, 214 and is disposed through the eyelet 118, 218 of each lobe 116, 216 to maintain the expandable occlusion tip 114, 214 in the unexpanded or undeployed and folded state until delivery and deployment wherein the expandable occlusion tip 114, 214 expands to the expanded state at a treatment site. As discussed above, in these embodiments, each lobe 116, 216 extends at respectively different distances so as to allow the retention device or guidewire 23 to more easily thread through each eyelet 118, 218 of each lobe 116, 216 respectively. In other embodiments, one or more of the lobes 116, 216 of the expandable occlusion tip 114, 214 may extend at the same distance if desired.

Figure 7:
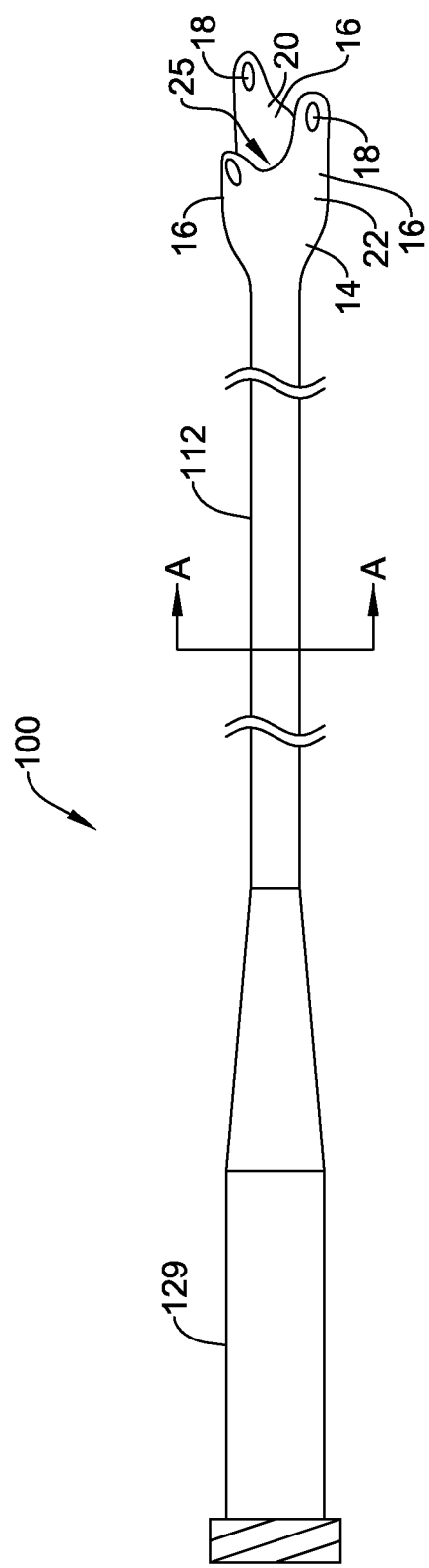
FIG. 7 is a side view of an example medical device.

FIG. 7 is a side view of an exemplary medical device 100 including a catheter shaft 112 that may be employed in combination with the expandable occlusion tip 14 disclosed herein. A hub 129 may be attached to the catheter shaft 112. The medical device 100 may be used for a number of different interventions. For example, the medical device 100 may be a catheter that can be used for intravascular procedures (including cardiac procedures, peripheral procedures, and neural procedures). In some embodiments, the medical device 100 may also be used to inject contrast materials (e.g., including injection of contrast materials at increased pressures), deliver embolic agents (e.g., microspheres, particles with low friction, etc.), other therapeutic agents, and the like. The medical device 100 may also be employed to reduce or remove material from a vessel or organ, for example for reducing thrombus in an artery, for example, with a vacuum using negative relative pressure.

The materials that can be used for the various components of the catheter 10 (and/or other medical devices and/or catheter shafts disclosed herein) may include those commonly associated with medical devices. For simplicity purposes, the following discussion makes reference to the catheter shaft 12, the expandable occlusion tip 14, and other components of the catheter 10. However, this is not intended to limit the devices and methods described herein, as the discussion may be applied to other similar tubular members and/or components of tubular members or devices disclosed herein, some of which are discussed in more detail below.

The catheter shaft 12 and/or other components of medical device may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Figure 8:
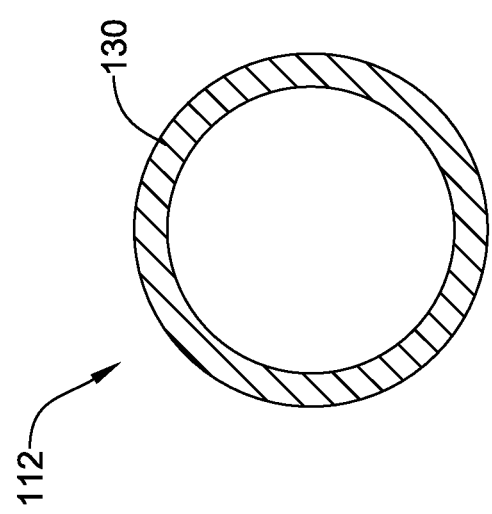
FIG. 8 is a cross-sectional view of an example medical device taken at section A-A of FIG. 7.

In some embodiments, the catheter shaft 112 may include a single polymeric layer 130 as shown in FIG. 8.

Figure 9:
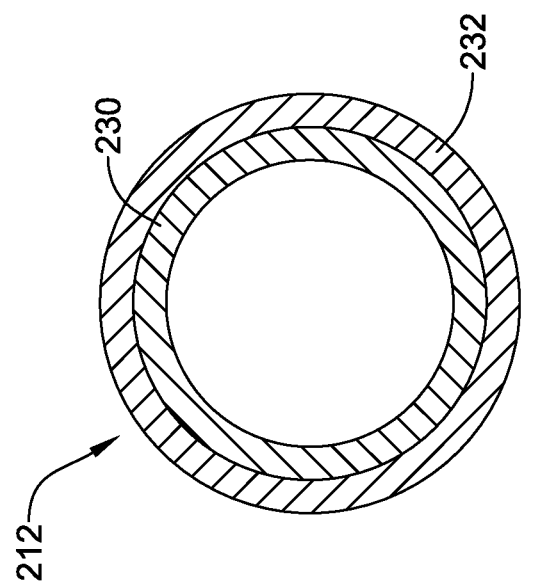
FIG. 9 is a cross-sectional view of an example medical device taken at section A-A of FIG. 7.

In at least some embodiments, a catheter shaft 212 may include a plurality of layers. For example, FIG. 9 illustrates the catheter shaft 212 having an inner liner or layer 230, for example, a polymeric layer, and an outer reinforcing layer 232. In some embodiments, the catheter shaft 212 is formed from a polyether-block-amide copolymer having a wire braided reinforcement layer.

Figure 10:
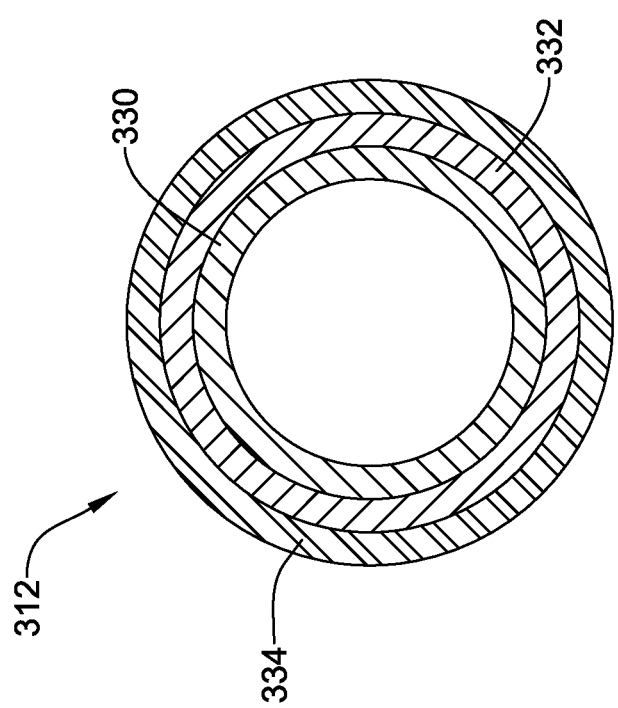
FIG. 10 is a cross-sectional view of an example medical device taken at section A-A of FIG. 7.

FIG. 10 illustrates a catheter shaft 312 having an inner liner or layer 330, for example, a polymeric layer, an intermediate layer 332, for example a reinforcing layer, or a tie layer to improve adhesion between the inner layer 330 and an outer layer 334. The intermediate layer 332 may be, for example, another polymeric layer.

The inner liner 230, 330 in any of the above embodiments may include lubricious material such as polytetrafluoroethylene (PTFE), etched PTFE, fluorinated ethylene propylene (FEP), high density polyethylene (HDPE), ultra high density polyethylene (UHDPE), ultra high molecular weight polyethylene (UHMWPE), or the like. Other materials are contemplated including those disclosed herein. The outer layer 334 in any of the embodiments disclosed herein may include one or more polymers such as polyether block amide, polyurethane, combinations or blends thereof, or the like. Other materials are contemplated including those disclosed herein.

The reinforcing layer 232, 332 may include a braid, coil, mesh, or other suitable reinforcement. In at least some embodiments, the reinforcing layer 232, 332 may include a polymeric braid. For example, the reinforcing layer 232, 332 may include an ultra-high molecular weight polyethylene braid or a liquid crystal polymer (LCP) braid such as a polyester LCP braid or an aromatic polyester LCP braid, an example of which are commercially sold under the tradename of Vectran®. Other materials and/or reinforcements are contemplated including those disclosed herein. In at least some embodiments, the melting temperature of the reinforcing layer 232, 332 may be less than the melting temperature of the liner 230, 330, the outer layer 334, or both.

All of the layers may extend along the full length of catheter shaft 212, 312. Alternatively, one or more of layers may extend along only a portion of the length of the catheter shaft 212, 312.

Figure 11:
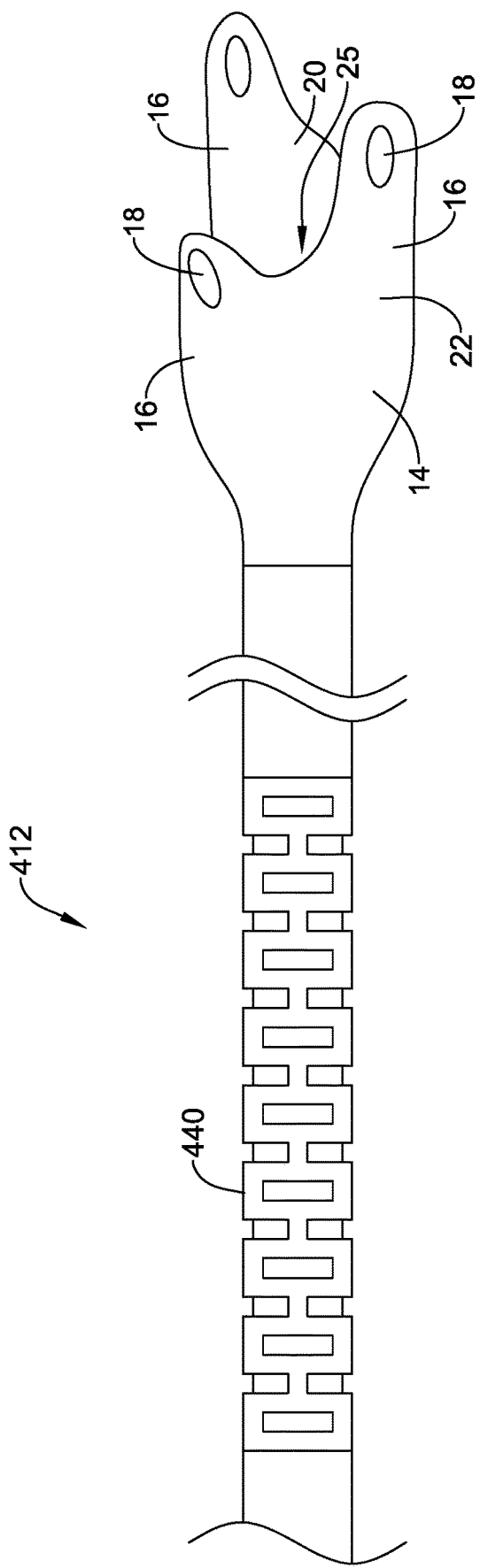
FIG. 11 is a side view of an example medical device.

The desired stiffness, torquability, lateral flexibility, bendability or other such characteristics can be imparted to the catheter shaft. For example, in FIG. 11, a catheter shaft 412 is shown having a plurality of apertures 440 such as grooves, cuts, slits, slots or the like, formed in a portion of, or along the entire length of the catheter shaft 412.

Catheter shafts of the types described with respect to FIGS. 6-8 can be found in commonly assigned US Patent Publication Nos. 2004/0193140 A1 and 2015/0057639 A1, is the entire contents of which are incorporated herein by reference.

Any suitable process can be used for manufacturing the catheter shaft 12 including extrusion. Extrusion may allow for relatively thin walled catheter shafts 12 to be manufactured. For example, the catheter shaft 12 may have a wall thickness as low as about 0.0001 to 0.001 inches (about 0.00254 mm to 0.0254 mm), or about 0.0001 to 0.0002 inches (about 0.00254 mm to 0.0508 mm), or about 0.00015 inches (about 0.00381 mm).

In general, the process may allow for catheter shafts 12 to be manufactured having relatively larger inner diameters while still maintaining relatively small outer diameters. The process may also result in relatively strong catheter shafts 12.

Manufacturing the catheter shaft 12 may also include using a mandrel, for example, when a liner 230, 330 is employed. The mandrel may vary in size, depending on the intervention. For example, the mandrel may be a silver coated copper core or other suitable mandrel with an outer diameter in the range of about 0.01 to 0.05 inches, or about 0.02 to 0.04 inches, or about 0.022 to 0.027 inches or so. In some embodiments, a reinforcing layer 232 may be disposed along the outer surface of the liner 230 as shown in FIG. 6. In other embodiments, the outer layer 334 may be disposed along the outer surface of the reinforcing layer 332 disposed on a liner 330 as shown in FIG. 7. The process for disposing layers onto the mandrel may include an extrusion process. When using an extrusion process, the assembly may be subjected to extrusion temperatures in the range of about 100 to 200° C., or about 120 to 190° C., or about 140 to 170° C. Multilayer shafts can be also achieved by using an overmolding a larger diameter extrusion onto a smaller diameter extrusion, shrinking wrapping the assembly, and placing it in an oven.

The expandable occlusion tip 14 may be formed by molding, for example, injection molding, and disposed on the catheter shaft 12 such as by adhesion or welding, for example. If a metal frame 118, 128 is employed in forming the expandable occlusion tip 14, the metal frame 118, 128 may be first placed in a mold, for example, an injection mold, and then the expandable occlusion tip 14 is molded over the frame 118, 128 as discussed above.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in is other embodiments. The invention's scope is, of course, defined in the language in which the appended claims are expressed.

What is claimed is:

1. A method of treating a body lumen, the method comprising:
    advancing a catheter through the body lumen toward a treatment site, the catheter comprising an elongated tubular member including a proximal portion and a distal portion and a lumen and the distal portion of the elongated tubular member comprising an expandable occlusion tip, the expandable occlusion tip comprising a plurality of lobes, each of the plurality of lobes comprising an eyelet, the expandable occlusion tip having an unexpanded configuration, in the unexpanded configuration the plurality of lobes extend distally from the elongated tubular member, and a guidewire extending through the lumen of the elongated tubular member and into the eyelet of each of the plurality of lobes;
    wherein the guidewire extends through the eyelet of each of the plurality of lobes to hold the expandable occlusion tip in the unexpanded configuration; and
    retracting the guidewire to shift the expandable occlusion tip from the unexpanded configuration to an expanded configuration to radially expand the plurality of lobes to restrict flow.

2. The method of claim 1 further comprising injecting a contrast fluid, an embolent, a therapeutic agent or combinations thereof during the advancing step and while the expandable occlusion tip is in the unexpanded configuration.

3. The method of claim 1 comprising pre-loading the guidewire in the elongated tubular member through the expandable occlusion tip and into the eyelet of each of the plurality of lobes.

* * * * *